US008450359B2

(12) United States Patent
McCoy et al.

(10) Patent No.: US 8,450,359 B2
(45) Date of Patent: May 28, 2013

(54) POLYMER-SUPPORTED PHOTOSENSITIZERS FOR THE GENERATION OF SINGLET OXYGEN

(75) Inventors: Colin P. McCoy, Belfast (GB); Sean P. Gorman, Belfast (GB); David S. Jones, Belfast (GB); Steven E. J. Bell, Belfast (GB)

(73) Assignee: The Queen's University of Belfast, Belfast (GB)

( * ) Notice: Subject to any disclaimer, the term of this patent is extended or adjusted under 35 U.S.C. 154(b) by 807 days.

(21) Appl. No.: 12/278,008

(22) PCT Filed: Feb. 5, 2007

(86) PCT No.: PCT/GB2007/000387
§ 371 (c)(1),
(2), (4) Date: Dec. 10, 2008

(87) PCT Pub. No.: WO2007/088392
PCT Pub. Date: Aug. 9, 2007

(65) Prior Publication Data
US 2009/0292357 A1    Nov. 26, 2009

(30) Foreign Application Priority Data
Feb. 3, 2006    (GB) .................................. 0602125.7

(51) Int. Cl.
*A61K 31/40*    (2006.01)
(52) U.S. Cl.
USPC ............................ 514/410; 514/185; 540/145

(58) Field of Classification Search
USPC .................... 525/332, 383; 204/157; 514/410
See application file for complete search history.

(56) References Cited

U.S. PATENT DOCUMENTS

| | | | | |
|---|---|---|---|---|
| 4,008,136 A * | 2/1977 | Williams | ................. | 210/748.08 |
| 4,104,204 A * | 8/1978 | Williams | ................. | 521/32 |
| 4,315,998 A * | 2/1982 | Neckers et al. | ............. | 525/359.3 |
| 4,318,883 A * | 3/1982 | Polony et al. | .................... | 422/22 |
| 4,413,070 A * | 11/1983 | Rembaum | ..................... | 523/223 |
| 4,499,154 A * | 2/1985 | James et al. | .................... | 428/494 |
| 4,575,476 A * | 3/1986 | Podell et al. | .................... | 428/494 |
| 4,666,824 A * | 5/1987 | Messer | ......................... | 430/325 |
| 4,915,804 A * | 4/1990 | Yates et al. | ................. | 204/157.5 |
| 4,921,589 A * | 5/1990 | Yates et al. | ................. | 204/157.5 |
| 5,109,016 A * | 4/1992 | Dixon et al. | .................. | 514/410 |
| 5,127,706 A * | 7/1992 | Clark | ........................ | 297/188.06 |
| 5,192,788 A * | 3/1993 | Dixon et al. | .................. | 514/410 |
| 5,236,914 A * | 8/1993 | Meunier et al. | ............... | 514/185 |
| 5,523,134 A * | 6/1996 | Strong | ......................... | 428/35.2 |
| 5,900,346 A * | 5/1999 | Sinta et al. | .................. | 430/270.1 |
| 5,955,256 A * | 9/1999 | Sowemimo-Coker et al. | ... | 435/2 |

(Continued)

FOREIGN PATENT DOCUMENTS

DE    19935179 A1 *    2/2001
EP    0032443 A2        7/1981

(Continued)

*Primary Examiner* — James J Siedleck
*Assistant Examiner* — Peter A Salamon
(74) *Attorney, Agent, or Firm* — Pepper Hamilton LLP

(57) ABSTRACT

A material comprising at least one polymer and at least one sensitizer wherein the sensitizer is localised at a surface of the material wherein the sensitizer is an agent or compound able to provide improved anti-bacterial and/or anti-viral activity following exposure of the sensitizer to a particular wavelength or range of wavelengths of electromagnetic radiation.

15 Claims, 7 Drawing Sheets

U.S. PATENT DOCUMENTS

| | | | |
|---|---|---|---|
| 5,965,319 A * | 10/1999 | Kobayashi | 430/176 |
| 6,005,032 A * | 12/1999 | Austin | 524/82 |
| 6,107,480 A * | 8/2000 | Funken et al. | 540/145 |
| 6,239,048 B1 * | 5/2001 | Wilson et al. | 442/123 |
| 6,420,455 B1 * | 7/2002 | Landgrebe et al. | 523/122 |
| 6,545,102 B1 * | 4/2003 | Akhavan-Tafti et al. | 525/340 |
| 6,630,128 B1 * | 10/2003 | Love et al. | 424/9.362 |
| 6,649,683 B2 * | 11/2003 | Bell | 524/440 |
| 6,774,249 B2 * | 8/2004 | Akhavan-Tafti et al. | 549/510 |
| 6,936,316 B2 * | 8/2005 | Nigam et al. | 428/32.17 |
| 7,230,040 B1 | 6/2007 | Carlo et al. | |
| 2003/0095916 A1 * | 5/2003 | Akhavan-Tafti et al. | 423/579 |
| 2005/0112650 A1 * | 5/2005 | Chang et al. | 435/6 |
| 2005/0131356 A1 * | 6/2005 | Ash et al. | 604/265 |
| 2005/0244647 A1 * | 11/2005 | Droschel et al. | 428/412 |
| 2007/0238660 A1 * | 10/2007 | Michielsen et al. | 514/12 |
| 2008/0275033 A1 | 11/2008 | Brown et al. | |
| 2009/0292357 A1 * | 11/2009 | McCoy et al. | 623/6.56 |

FOREIGN PATENT DOCUMENTS

| | | |
|---|---|---|
| EP | 0624455 | 11/1994 |
| EP | 0891977 A1 | 1/1999 |
| WO | WO 89/11277 | 11/1989 |
| WO | WO 93/00815 A1 | 1/1993 |
| WO | WO 99/49823 | 10/1999 |
| WO | WO 00/12512 A1 | 3/2000 |
| WO | WO 03027007 A1 * | 4/2003 |
| WO | WO 2004/056828 | 7/2004 |
| WO | WO 2005/065731 A1 | 7/2005 |
| WO | WO 2006/000765 | 1/2006 |
| WO | WO 2007/114843 A2 | 10/2007 |

\* cited by examiner

POLYMER-SUPPORTED PHOTOSENSITIZERS FOR THE GENERATION OF SINGLET OXYGEN

CROSS REFERENCE TO RELATED APPLICATIONS

This application is a U.S. national stage filing under 35 U.S.C. §371 of PCT Application PCT/GB2007/000387 filed Feb. 5, 2007, which claims priority to GB 0602125.7 filed Feb. 3, 2006.

The present invention relates to materials which include a sensitizer, in particular materials including a sensitizer which may be used to form a medical device.

BACKGROUND

Materials comprising polymer (wherein a polymer may include a mixture of polymers) are widely used to provide a range of products, for example products for use in storage of liquids and solids, food preparation and storage, healthcare apparatus, medical devices and the like. Bacterial adherence to a surface of a material and subsequent proliferation of said bacteria presents a risk of infection.

Bacterial adherence to the surface of a material which forms a medical device is a particular problem and can lead to complications following surgery using said medical device, for example wound abnormalities, which may require prolonged hospitalisation, antibiotic therapy and/or further surgery. These complications cause significant costs for healthcare systems.

In these identified uses and others, it would be advantageous to provide a material comprising at least one polymer wherein said material has an anti-bacterial and/or anti-viral property or activity, particularly when said property of activity may be activated or enhanced as desired.

SUMMARY OF THE INVENTION

According to a first aspect of the invention there is provided a material comprising at least one polymer and at least one sensitizer wherein said sensitizer is localised at a surface of the material and wherein said sensitizer provides increased anti-bacterial and/or anti-viral activity following exposure of the sensitizer to electromagnetic radiation.

Localising the sensitizer at a surface of the material is advantageous as this is the portion of the material most likely to come into contact with bacteria or virus. The localisation of sensitizer at a material's surface is advantageous over incorporation of sensitizer into the bulk of a material, as sensitizer within the bulk of a material is mostly inactive, as it is unable to cause singlet oxygen production. Localisation of a sensitizer at a surface of a material therefore does not require erosion or degradation of the material to allow the sensitizer to become active.

Suitably, in embodiments of the invention localisation of a sensitizer at a surface of a material includes coating of a surface of a material with sensitizer to form a coating surface layer of a sensitizer on the material. Suitably in said embodiments or alternative embodiments localisation of a sensitizer at a surface of a material includes incorporating sensitizer in a surface layer(s) of a material.

Suitably the material of the present invention may have a sensitizer imbibed in a surface layer where the sensitizer, when activated, produces singlet oxygen, which gives an antimicrobial and/or anti-viral effect.

Localisation of a sensitizer at a surface of a material may be via physical or chemical interactions of a sensitizer with a surface of the material. Suitably, localisation may be by physical interaction only, for example electrostatic interaction of a sensitizer with a suitable polymer present in the material. This provides a general method of localising a sensitizer at a surface.

Advantageously, the surface of the material may not need to be chemically modified such that the chemical structure of the surface of the material is altered, other than the ionisation state of ionisable groups of a polymer present in the material, to allow a sensitizer to be provided at, for example on or in, a surface of the material. In particular, the material of the present invention may not require the presence of an additional covalently bound ionisable moiety at the surface of the material to allow a sensitizer to be localised at a surface of the material.

In particular embodiments of the invention, on exposure of the sensitizer to electromagnetic radiation, for example, but not limited to visible light, the sensitizer produces highly reactive singlet oxygen $^1O_2$ which provide an anti-bacterial and/anti-viral effect.

Suitably, localisation includes the provision of sensitizer on the surface of a material and in the surface layers of a material, for example the material of the present invention may include sensitizer either mixed within the material at a surface layer of the material or provided as a coating layer on a surface of the material.

Suitably the sensitizer may be localised at a surface layer of thickness in the range 10 nm to 1 mm.

In particular embodiments a sensitizer may be localised at a surface layer of thickness in the range 1 to 200 µm. In specific embodiments a sensitizer may be localised at a surface layer of thickness in the range 1 to 50 µm.

As will be appreciated by those of the art, where the sensitizer is able to permeate the material, the sensitizer may be applied to the surface of the material whilst not altering the material's surface shape or structure. In such cases, the material may not gain thickness following application of the sensitizer; however, the material will have a thickness in which the sensitizer is located.

Suitably said at least one sensitizer is selected from at least one of the groups comprising: phthalcyanines and metallophthalocyanines, for example, cationic water-soluble pyridinium zinc phthalocyanine (PPC), sulphonated phthalocyyanines and sulphonated metallocyanines; chlorins, for example, 5,10,15,20-Tetra(m-hydroxyphenyl)chlorin (m-THPC, "Foscan"); 5-Aminolaevulinic acid (ALA) and its derivatives; texaphyrins, sapphyrins, purpurins, for example, tin etiopurpyrin ("Purlytin"); porphyrin; or methylene blue and other dyes, for example, rose bengal, known in their electronic excited state to sensitize the production of singlet oxygen.

As will be appreciated by those of skill in the art, a combination of sensitizers may be used. A combination of sensitizers may be chosen so as to enhance the anti-bacterial and/or anti-viral activity of the material, to allow the anti-bacterial and/or anti-viral activity to be enhanced by specific or different wavelengths of electromagnetic radiation, or to lower costs or facilitate production of a material capable of providing an adequate level of singlet oxygen.

In preferred embodiments the at least one sensitizer may be a porphyrin.

Preferably wherein the at least one sensitizer is a porphyrin, the porphyrin may be selected from at least one: protoporphyrin IX, tetra-4-N-methylpyridinium porphyrin (TMPyP), tetra-4-sulfonato-phenyl porphyrin (TTPS), tetra (4N,N,N-trimethyl-anilinium)porphine tetrachloride (TMAP), haematoporphyrin derivative (HpD) and purified fractions such as "Photofrin".

A particular type of porphyrin may be advantageously selected for incorporation in or on a material by considering the substituents of the porphyrin needed for incorporation into or onto the material since the aromatic core of the porphyrin molecule is typically relatively undisturbed by peripheral substitution and will therefore likely retain photosensitising properties irrespective of the substitution around it.

In particularly preferred embodiments the porphyrin may be selected from at least one of tetra-4-N-methylpyrinium porphyrin (TMPyP) and tetra-4-sulfonato-phenyl porphyrin (TTPS). These porphyrins have a high overall charge and may be readily prepared in high purity.

The material of the present invention includes at least one polymer wherein said at least one polymer is selected from at least one natural or biopolymer for example, but not limited to, hydroxyapatites, keratin, or collagen or the like which may be suitable for use in scaffold constructs or in tissue engineering or a synthetic polymer.

In particular embodiments, the material may include at least one polymer selected from, but not limited to: polyolefins, for example, poly(ethylene), poly(propylene); vinyl polymer and copolymers, for example, poly(vinyl chloride), poly(vinyl pyrrolidoone); acrylate polymer and copolymers, for example, poly(2-hydroxyethyl methacrylate), poly(methyl methacrylate), poly(methacrylic acid), poly(acrylic acid), poly(diethylaminoethylmethacrylate), poly(diethylaminoethylethacrylate); elastomer, for example, silicone, styrene-isoprene/butadiene-styrene, latex; polyurethane; polyester, for example, poly(lactic acid), poly(glycolic acid), poly(caprolactone), poly(orthoesters); polyphosphazines or blends of said polymers herein. In particular embodiments the material may include a blend of silicone and acrylate polymers.

The material of the present invention is particularly advantageous for use in biomaterial. Biomaterial is material intended to interface with biological systems and may be used to manufacture prosthesis, an implant, and/or a surgical instrument. Suitably said biomaterials are biocompatible (the materials do not react with physiological components) and/or biostable (the materials do not degrade in response to contact with physiological components, for example blood).

In particularly preferred embodiments the material includes at least one polymer which is a hydrogel.

Suitably a hydrogel may be selected from one of poly(methacrylic acid-co-hydroxyethylmethacrylate), poly(diethylaminoethylmethacrylate-co-hydroxyethylmethacrylate) or poly(hydroxyethimethcacrylate-co-protoporphyrin).

As indicated above, it may be advantageous if the anti-bacterial and/or anti-viral activity of the sensitizer localised on or in a surface of the material of the invention may be increased in response to electromagnetic radiation. Suitably, such electromagnetic radiation may be provided by natural sources, for example daylight, or non-natural sources, for example an artificial light source, such as, but not limited to, a halogen lamp, a mercury vapour lamp, a tungsten lamp or a gas discharge/phosphor lamp. In particular cases, a suitable waveguide, for example, but not limited to, a fibre optic may be used to deliver suitable electromagnetic radiation to the material.

In one embodiment a sensitizer may be inactive as an anti-microbial and/or an anti-viral until the at least one sensitizer is exposed to electromagnetic radiation of a particular range of wavelengths, for example visible light.

In another embodiment the at least one sensitizer may have activity as an anti-microbial and/or anti-viral when not exposed to electromagnetic radiation of a particular range of wavelengths, but show increased activity following exposure to electromagnetic radiation of a particular range of wavelengths, for example light. In such an embodiment the sensitizer may provide continuous anti-microbial and/or anti-viral activity which may be enhanced by exposure of the material to electromagnetic radiation. This may be advantageous when, for example, the material is included in an intra-ocular lens wherein, in use, in the dark when the patient's eye lids are shut the anti-bacterial and/or anti-viral activity is present and this activity is enhanced on exposure of the lens to light, for example when the patient's eye lids are open.

Photodynamic therapy in which a sensitizer in or on a material may be activated by electromagnetic radiation allows anti-microbial and/or anti-viral activity to be provided at a location where it is desired, for example the surface of a material which would be the most likely point bacterial colonisation would occur on the material.

Advantageously, the inclusion of a sensitizer in or on a material provides the material with improved therapeutic or prophylactic properties. Material of a first aspect of the invention may be used to reduce bacterial or viral colonisation of a treatment area. Accordingly, the invention provides a method of reducing bacterial or viral colonisation of a treatment area, comprising the steps:

providing a material according to a first aspect of the invention, and providing electromagnetic radiation of a suitable wavelength to cause the material to produce highly reactive singlet oxygen.

Suitably the above method may be performed in vitro or in vivo.

As will be appreciated, the material of the present invention may be formed from or have been applied to a device for use in the method.

Electromagnetic radiation may be provided to a material which, in use, is located in the body of an animal, preferably a human. For example, a light source may by provided to a material located in the body via an optic fibre. This may be as part of a catheter assembly. This may be advantageous as the treatment area at which the sensitizer may act is localised at the required point and minimises the risk of accumulation of sensitizer in normal tissue.

Alternatively, material located in the body may be provided with electromagnetic radiation by providing a suitable electromagnetic radiation source outside the body and directing the electromagnetic radiation towards the site of the material. For example, a lamp which produces the right wavelength of radiation may be provided to any part of the body through which that radiation can be delivered such that radiation generated by the lamp directed towards material located in the body under the skin receives the radiation.

Suitably a sensitizer of a material of the present invention provides increased anti-bacterial and/or anti-viral activity following exposure of the sensitizer to electromagnetic radiation in the range 200 nm to 750 nm. Suitably, anti-bacterial and/or anti-viral activity is enhanced by at least 10 fold, at least 50 fold, at least 100 fold, preferably at least 200 fold, more preferably at least 500 fold, yet more preferably at least 750 fold and most preferably 1000 fold.

Suitably a sensitizer of a material of the present invention provides increased anti-bacterial and/or anti-viral activity following exposure of the sensitizer to electromagnetic radiation in the range 300 nm to 700 nm. In particular embodiments a sensitizer of a material of the present invention provides increased anti-bacterial and/or anti-viral activity following exposure of the sensitizer to electromagnetic radiation in the visible light range, in the range 390 nm to 450 nm or in the range 415 nm to 430 nm.

Suitably on exposure of a sensitizer to a particular range of wavelengths of electromagnetic radiation the sensitizer produces highly reactive singlet oxygen $^1O_2$.

The singlet oxygen provided by the sensitizer may exist for around 1 to 50 microseconds. In particular embodiments, the singlet oxygen provided may exist for $10^{-5}$ to $10^{-7}$ seconds. In specific embodiments, the singlet oxygen provided may exist for $10^{-5}$ to $10^{-6}$ seconds.

A lifetime restricted to the range $10^{-5}$ to $10^{-6}$ seconds limits the effective distance between the initial excitation event and the anti-microbial and/or anti-viral effect of the sensitizer to a few micron from the position of the sensitizer in the material and thus localises the action of the sensitizer to a treatment area.

Suitably, the restriction of the lifetime of a singlet oxygen means that, in use, the sensitizer may not enter a cell.

In particular embodiments the at least one sensitizer may be electrostatically bound to the at least one polymer present in the material. Alternatively, the sensitizer may be covalently bound to at least one polymer of the material. Suitably, this may be achieved without prior modification of the material.

According to a second aspect of the present invention there is provided a device comprising the material according to the first aspect of the invention.

Suitably the device may be provided with the material on at least one surface of the device.

Where the device is for example tubing, the device may be formed of the material of the present invention such that an external or internal surface, or indeed both surfaces, of the tubing are provided with sensitizer. Alternatively, or additionally, the material of the present invention may be applied to a surface of the tubing, for example an internal surface, as a coating to provide a sensitizer to the internal surface.

As will be appreciated by those of skill in the art, where a device comprises multiple internal surfaces, for example where a device has a honeycomb structure with internal voids or comprises beads wherein said beads have external surfaces internal to the surface of the complete device, material of the present invention may be provided to the surfaces forming the internal voids or the external surfaces of said beads. In particular embodiments, internal voids of a device may be filled with the material of the present invention such that the material is stored within the device and may be supplied to the surface(s) of the device over a period of time.

Suitably anti-bacterial and/or anti-viral activity is retained throughout the lifetime of the device.

Suitably, in particular embodiments, the device may be selected from urinary tract devices (including ureteral stents and urinary catheters); ocular devices (including contact lenses); ocular lens storage containers; orthopaedic devices; respiratory devices; cardiovascular devices; dental devices; neurological devices; gastrointestinal devices; audiology devices; surgical devices; including surgical gloves; foot care devices; wound healing devices; condoms; blood bags; blood administration tubing; extracorporeal membrane oxygenation equipment; dialysis and peritoneal drainage bags; apheresis equipment; urinary collection bags; urological catheters; wound drainage bags and tubes; enteral feeding equipment; nasogastric tubes; breast pump tubes; intravenous catheters; drip chambers; tubing and solution bags; total parenteral nutrition bags; hemodialysis tubing and catheters; film wrap; gloves; endotrachael tubes; tracheostomy tubes; esophagel tubes; humidifiers; ocular prosthesis; or sterile water bags and tubing.

In embodiments of the invention, the above and further devices, for example subcutaneous implants, pessaries, suppositories, intravaginal devices, intrauterine devices, intrarectal devices, transdermal devices, wound care devices and the like may have drug delivery functions i.e. permit drug delivery from the device over a period of time.

Preferably a device of the invention may be a medical device. Suitably a medical device may be selected from devices suitable for temporary or permanent implantation in, or for attachment in or on, the human or animal body, the device being selected from, but by no means limited to, urinary tract devices (including ureteral stents and urinary catheters), ocular devices (including contact lenses), orthopaedic devices, respiratory devices, cardiovascular devices, dental devices, neurological devices, gastrointestinal devices, audiology devices, surgical devices, foot care devices, wound healing devices, condoms, subcutaneous implants, pessaries, suppositories, intravaginal devices, intrauterine devices, intrarectal devices, transdermal devices, wound care devices and the like.

More preferably the medical device may be a prosthesis. In particular embodiments a prosthesis may be selected from an intraocular lens and/or a contact lens. In such an embodiment the sensitizer may be chemically or physically bound to the surface of the intra-ocular lens such that the sensitizer does not enter a cell or localise on a cell membrane.

Suitably there is provided a contact lens or an intra-ocular lens comprising the material of the first aspect of the invention.

Suitably no prior chemical modification step of the surface of a prosthesis, preferably an intra-ocular lens or contact lens, is required to allow localisation of a sensitizer at a surface of the prosthesis. Preferably a prosthesis, for example, an intra-ocular lens or a contact lens may be formed from hydrogel. Advantageously, a sensitizer may be chemically or physically bound to said hydrogel without prior chemical modification of said hydrogel.

In a particular embodiment of a device of the present invention, the device may be an intra-ocular lens or a contact lens including a porphyrin sensitizer. Suitably a porphyrin sensitizer may be at least one porphyrin selected from the group comprising: protoporphyrin IX, tetra-4-N-methylpyridinium porphyrin (TMPyP), tetra-4-sulfonato-pheynl porphyrin (TTPS), tetra(4N,N,N-trimethyl-anilinium)porphine tetrachloride (TMAP), haematoporphyrin derivative (HpD) and purified fractions such as "Photofrin".

According to a third aspect of the present invention there is provided a process of manufacturing a material comprising at least one polymer and at least one sensitizer wherein said process comprises the steps of:

providing a charged sensitizer to a charged surface of a material comprising polymer,
providing suitable conditions to cause an electrostatic interaction between the sensitizer and the surface of the material, and
binding the sensitizer to the charged surface.

Suitably the charged surface may include a charged polymer selected from poly(methacrylic acid), poly(acrylic acid), poly(diethylaminoethylmethacrylate), poly(diethylaminoethylacrylate, poly(lactic acid), poly(glycolic acid), copolymers of these with neutral acrylates, or charged biopolymers such chitosan.

Preferably the charged surface may include a charged polymer selected from poly(methacrylic acid) or poly(acrylic acid) or poly(diethylaminoethylmethacrylate) or poly(diethylaminoethylethacrylate and copolymers of same with poly(hydroxyethylmethacrylate) or poly(methylmethacrylate).

In particular embodiments the charged surface may include at least one charged polymer selected from a hydrogel comprising poly(methacrylic acid) and copolymers of same with poly(hydroxyethylmethacrylate).

Suitably, at least one charged sensitizer may be selected from tetra-4-N-methylpyrinium porphyrin (TMPyP), tetra-4-sulfonato-phenyl porphyrin (TTPS), tetra-(4-N,N,N-trimethyl-anilinium)porphine tetrachloride (TMAP), tetra-(p-hydroxyphenyl) porphyrin, tetra-(p-aminophenyl) porphyrin, phthalocyanine tetrasulfonic acid and their metal salts; haematoporphyrin derivative (HpD); purified fractions such as "Photofrin" and related sulfonato-, pyridyl-, amino- and carboxylato-substituted porphyrins and phthalocyanines.

In particular embodiments, at least one charged sensitizer may be selected from tetra-4-N-methylpyrinium porphyrin (TMPyP) and tetra-4-sulfonato-phenyl porphyrin (TTPS).

Suitably, a sensitizer is provided to a charged surface including polymer by immersing the surface in a solution including a sensitizer. Suitably the time of immersion of the surface ranges from 1 s to 24 hours, 1 s to 12 hours, 1 s to 6 hours, 1 s to 1 hour, 10 s to 10 minute, 1 minute to 5 minute or 1 s to 1 min.

Suitably a sensitizer may be provided to a surface at a concentration in the range 0.1 to 50 mg/ml, suitably in the ranges 1 to 5 mg/ml, 10 to 50 mg/ml or 0.1 to 0.5 mg/ml as appropriate.

Advantageously this process is typically a straightforward and effective method of loading controlled amounts of the sensitizer at or to or in a surface of a material comprising polymer.

Suitably, binding includes chemical and/or physical interaction of a sensitizer with polymer of the material. In particular embodiments binding may be the physical interaction of a sensitizer with a polymer of the material, for example by electrostatic interaction.

In one embodiment the sensitizer is negatively charged and the surface of the material is positively charged.

In an alternative embodiment the sensitizer is positively charged and the surface of the material is negatively charged.

According to a fourth aspect of the invention there is provided a process of manufacturing a material comprising at least one polymer and at least one sensitizer wherein said process comprises the steps of:
  functionalising at least one of a surface of a material comprising polymer to which the sensitizer is to be bound,
  providing a sensitizer to a surface of the material, and
  binding the sensitizer to the surface of the material.

Suitably the polymer of the material may be functionalised by attaching a non-ionisable moiety to the surface of the material before binding of a sensitizer to a surface of the material.

Suitably, a sensitizer may be provided to a polymer by immersing the polymer in a solution including a sensitizer. Suitably immersion may range in time from 1 s to 24 hours, 1 s to 12 hours, 1 s to 6 hours, 1 s to 1 hour, 10 s to 10 minute, 1 minute to 5 minute or 1 s to 1 min.

Suitably a sensitizer may be provided to a polymer at a concentration in the range 0.1 to 50 mg/ml, 1-5 mg/ml, 10 to 50 mg/ml or 0.1 to 0.5 mg/ml as appropriate.

Suitably said process according to the fourth aspect of the present invention further comprises a step of initiating free radical polymerisation of the polymer by heating the polymer and the sensitizer.

According to a fifth aspect of the invention there is provided a process of manufacturing a material comprising at least one polymer and at least one sensitizer wherein said process comprises the steps of:
  dissolving a neutral sensitizer into solvent in which the sensitizer is soluble in sufficient quantity to perform the process,
  immersing a neutral polymer in this solution of dissolved neutral sensitizer in solvent, and
  providing reaction conditions such that the at least one sensitizer binds to the at least one polymer.

Suitably binding includes chemical and/or physical interaction between the sensitizer and the polymer. In particular embodiments binding consists of physical interaction, for example, but not limited to hydrophobic interaction, or electrostatic interaction.

Suitably, as the sensitizer is neutral, the solvent may be chosen from lower dielectric constant solvents. Suitably the solvent may be at least one solvent selected from hexane, dichloromethane, chloroform, ethyl acetate, acetone, pentane, methyl ethyl ketone, acetonitrile, diethyl ether.

Suitably, this process exploits sensitizer solubility in polymers for incorporation of neutral sensitizers in neutral polymers.

In particular embodiments at least one solvent may be selected from dichloromethane, diethyl ether, or chloroform. Preferably the solvent may be dichloromethane.

Suitably, at least one neutral polymer which may be employed in the process may be selected from vinyl and acrylate polymers and copolymers, polyethylene, polypropylene, poly(vinyl alcohol), poly(methyl methacrylate), poly(methyl acrylate), poly(hydroxyethylmethacrylate), poly(vinyl chloride); elastomers, for example, silicone, styrene-isoprene/butadiene-styrene, latex; polyurethanes; polyesters, poly(caprolactone), poly(orthoesters); polyphosphazines; or biopolymers such as keratin and collagen.

In particular embodiments at least one neutral polymer which may be employed in the process may be selected from poly(hydroxyethylmethacrylate) and copolymers with other neutral acrylates, silicones, poly(vinyl chloride) or a blend of silicone and acrylate polymers.

Preferably at least one neutral polymer which may be employed in the process may be selected from silicone and blends with acrylates.

At least one neutral sensitizer may be selected from the group phthalcyanines and metallophthalocyanines; chlorins, for example, 5,10,15,20-Tetra(m-hydroxyphenyl)chlorin (m-THPC, "Foscan"); 5-Aminolaevulinic acid (ALA) and its derivatives; texaphyrins, sapphyrins, purpurins, for example, tin etiopurpyrin ("Purlytin") or methylene blue.

Suitably a solvent may be removed from the process by evaporation.

Suitably, a sensitizer may be provided to a polymer by immersing the polymer in a solution including a sensitizer. Suitably immersion may range in time from 1 s to 24 hours, 1 s to 12 hours, 1 s to 6 hours, 1 s to 1 hour, 10 s to 10 minute, 1 minute to 5 minute or 1 s to 1 min.

Suitably the process may be conducted at a temperature range between the freezing and boiling point of the solvent used.

Suitably a sensitizer may be provided to a polymer at a concentration in the range 0.1 to 50 mg/ml, 1-5 mg/ml, 10 to 50 mg/ml or 0.1 to 0.5 mg/ml as appropriate.

In one particular embodiment of this process, protoporphyrin IX (PPIX), a neutral sensitizer, may be dissolved in dichloromethane at concentrations in the range 0.1 mg/ml to 20 mg/ml, 0.5 mg/ml to 10 mg/ml, 1 mg/ml to 5 mg/ml, or preferably 2 mg/ml.

In a specific embodiment, incorporation of a neutral sensitizer into a neutral silicone elastomer prepared with medical grade poly(dimethylsiloxane) (dimethicone) crosslinked with 2.5% w/w tetrapropoxysilane using either tin 2-ethylhexanoate or platinum as catalyst, either with or without 22% w/w silica filler, was achieved by immersion of the silicone elastomer into the PPIX solution for 60 seconds. This process produced a surface layer of PPIX of approximately 100 micron thickness. The thickness of the surface layer may be controlled by either altering the concentration of sensitizer solution or altering the time of immersion in sensitizer solution.

Suitably neutral polymer may be comprised of single or multiphase materials, for example material where one phase is a silicone-based material such as poly(dimethylsiloxane) or poly(methylhydrosiloxane) and the other phase is a hydrogel-based material such as 2-(hydroxyethyl) methacrylate.

Suitably in a process as described herein, the step of providing a sensitizer to a polymer or material including a polymer includes dipping a material comprising polymer into a sensitizer solution, or spraying a sensitizer solution onto a material comprising polymer. Suitably the thickness of a layer of sensitizer localised at a surface of a material may be controlled by altering the concentration of sensitizer solution and/or altering the time of contact of the sensitizer with the surface of the material.

Advantageously a process of the present invention allows for the concentration of a sensitizer in a surface layer on or in the material wherein said material comprises at least one polymer said method comprising the step of physically binding the sensitizer to the polymer.

Advantageously a process of the present invention does not require a pre-treatment step to bring about modification to the chemical structure of a polymer provided in the material, for example through the addition of an ionisable group, but only the charge of the surface to imbibe a sensitizer.

Physical binding includes interactions selected from hydrophobic bonding, electrostatic bonding, and hydrogen bonding.

Suitably the binding is by electrostatic interaction, for example Van der Waals forces, between the sensitizer and the polymer.

Suitably a process of the present invention may not require chemical modification of a surface of a material and/or polymer prior to binding sensitizer.

Suitably, a process of the present invention may further comprise at least one pre-treatment step selected from: immersing the material to which the sensitizer is to be bound in a solvent prior to binding of the sensitizer, drying out of the material or washing of the material.

Suitably a process of the present invention may further comprise a washing step following providing the sensitizer to remove any non-interacting sensitizer to minimise leaching of non interacting sensitizer.

Suitably a process of the present invention may further comprise a step of heating the material including the sensitizer localised thereon or therein a surface layer to initiate free radical polymerisation.

Suitably a process of the present invention may further comprise a step of providing the material formed by a process of the invention onto a surface of an intra-ocular lens or a surface of a contact lens.

Suitably a process of the present invention may further comprise a step of forming the material produced into an intra-ocular lens or contact lens from the material formed by the process.

In a particular embodiment of the present invention the sensitizer may be a vinyl-functionalised porphyrin (an example of which is protoporphyrin IX) which may be mixed with 2-hydroxyethylmethacrylate (HEMA) and dip or spin-coated onto a biomaterial. The coated material may then be heated to initiate free radical polymerisation to give a material with porphyrin covalently bound at a surface layer.

A sensitizer provided in or on a material of the first aspect of the invention may maintain, improve, or prolong the intended function or biocompatibility of a medical device comprising said material. Use of a sensitizer in or on a material may be beneficial in the treatment or prevention of disease in humans or animals by minimising bacterial and/or viral growth on the material.

Preferred features and embodiments of each aspect of the invention are as for each of the other aspects mutatis mutandis unless context demands otherwise.

Embodiments of the present invention will now be described by way of example only and with reference to the accompanying drawings in which.

Figure 8:
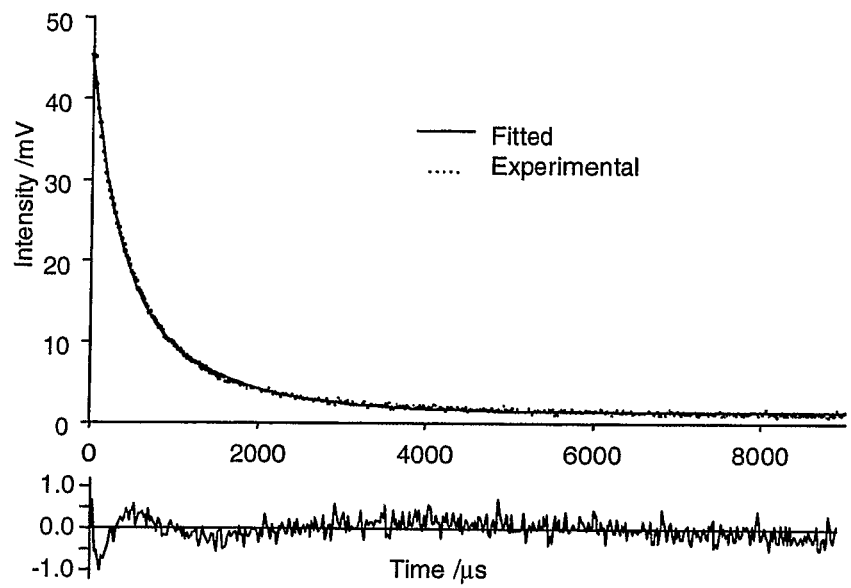
Figure 9:
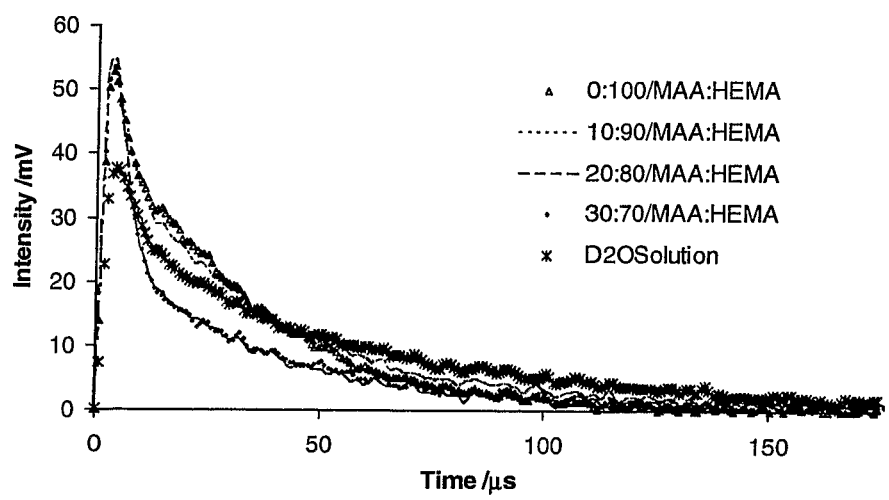

FIG. 8 illustrates transient absorbance difference signal ($\lambda_{ex}$=532 nm, $\lambda_{mon}$=474 nm) showing decay of excited TMPyP in 20:80/MAA:HEMA under $N_2$-bubbled conditions. The upper plot compares experimental data with a fitted biexponential decay. The lower plot shows the residuals to this biexponential fit; and FIG. 9 illustrates decay traces for $^1O_2$ (1270 nm) emission from four TMPyP-treated MAA:HEMA copolymers.

MICROBIOLOGICAL ACTIVITY OF PORPHYRIN SENSITIZERS

Studies were performed on the photosensitising activity of porphyrin solutions against *Staphylococcus epidermidis, Pseudomonas aeruginosa* and *Proteus mirabilis* as these organisms have been isolated from culture-positive cases of infectious endophthalmitis. Studies were performed by adding a porphyrin solution to a culture of the test organism, exposing this mixture to daylight or to a more intense light source comprising 4×250 W halogen bulbs, and then taking a 1 mL aliquot at certain times to determine the viable count.

Activity of three porphyrins, tetra(4N-methylpyridyl)porphine tetratosylate salt (TMPyP), tetra(4N,N,N-trimethylanilinium)porphine tetrachloride (TMAP) and tetra(4-sulfonatophenyl)-porphine dihydrochloride (TPPS) were examined.

TMAP has an identical porphyrin ring to TMPyP but bulkier substituent groups on the periphery of the ring.

10 mcg/mL solutions of the three porphyrins were investigated. Initially the solutions were made up at the desired concentration and then double filter sterilised. However, due to the ability of the porphyrin to stick to the filters, this reduced the concentration of the porphyrin present in the solution such that the concentrations of TMPyP, TPPS and TMAP studied were approximately 8.58 mcg/mL, 8.65 mcg/mL and 6.34 mcg/mL respectively.

24 Hour Studies

Inocula of approximately $1 \times 10^5$ cfu/mL were utilised throughout the microbiological studies of porphyrin solutions. Activity was examined both in normal daylight conditions and using a more intense light source comprising 4×250 W halogen bulbs, cooling the temperature to around 32° C.

*Pseudomonas aeruginosa*

TMPyP had no photosensitising activity in daylight. TMAP reduced growth by 1 log cycle at 24 hours. However, using the more intense light source, there was successful photoinactivation, providing complete kill, within 1 hour. For TPPS, there was one log cycle reduction in the viable count by 5 hours illumination with the more intense source.

*Staphylococcus epidermidis*

With TMPyP and TMAP there was successful photoinactivation, providing complete kill, within 1 hour in daylight but with TPPS 24 hours' illumination was required for successful inactivation. Using the more intense light source all organisms were photoinactivated, providing complete kill, within 1 hour.

*Proteus mirabilis*

Using daylight conditions there was 1 log cycle reduction in growth after 24 hours with TMPyP. TMAP yielded similar results, while TPPS showed no reduction in viable count over 24 hours. With the more intense light, TMPyP gave a three log cycle reduction in viable count by 5 hours, while TMAP gave a three log cycle reduction in 3 hours. TPPS did not show any photosensitising effect within 5 hours illumination.

The cationic porphyrins were more effective photosensitizers than the anionic TPPS.

Of the two cationic porphyrins, TMAP was more effective than the TMPyP, and also appeared to display some light independent activity.

The Gram-positive organism was more susceptible than the two Gram-negatives to photoinactivation by porphyrins.

One Hour Studies

For any of the porphyrin-organism combinations which showed complete photoinactivation, providing complete kill, by 1 hour in the 24 hour studies, further studies were performed in which samples were taken at 10, 20, 30, 40, 50 and 60 minutes. Unfiltered and double filter sterilised 10 mcg/mL solutions were used to examine the effect of double filtration on activity.

In daylight TMAP showed dark activity against *S. epidermidis* (there was no growth, including the dark control, even at 10 minutes illumination for the unfiltered solution, while the filtered solution was not active in the dark but showed similar activity in the light). It displayed no activity against *P. mirabilis* or *Ps. aeruginosa*.

In intense light, TMAP was active in light against *Ps. aeruginosa* by 30 minutes for the unfiltered solution and for the filtered solution. There was also some limited dark activity. TMAP was also active, both the filtered and the unfiltered solutions, in both dark and light, against *S. epidermidis* within 10 minutes.

In laboratory light, TMPyP was active against *S. epidermidis* both for the filtered and the unfiltered solutions within 10 minutes. The filtered solution appeared to have slightly more dark activity—within 30 minutes.

In intense light, TMPyP was active, for the unfiltered solution in the dark in 10 minutes and in 20 minutes for the filtered solution against *S. epidermidis*. It was active within 10 minutes illumination for both solutions. For *Ps. aeruginosa*, TMPyP was not active in the dark but in the light, both the filtered and the unfiltered solutions were active by 40 minutes.

In intense light, TPPS was active against *S. epidermidis* within 40 minutes illumination for the unfiltered solution and within 50 minutes for the filtered solution.

These studies indicate some light independent activity for TMPyP as well as TMAP.

Cationic TMAP and TMPyP are more active than anionic TPPS and that the Gram-positive organism is easier to photoinactivate, than a Gram-negative.

EXAMPLE 1

Incorporation of Sensitizer(s) Using Electrostatic Interaction

Figure 1:
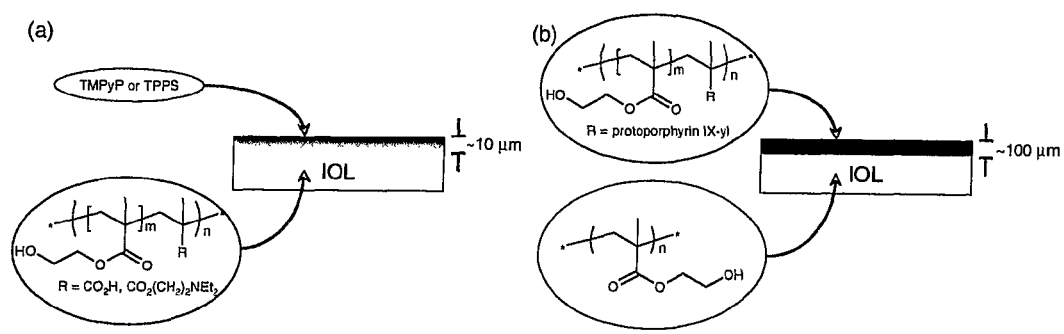
FIG. 1 illustrates two embodiments of incorporating porphyrin sensitizers as thin coatings on a material.
Figure 2:
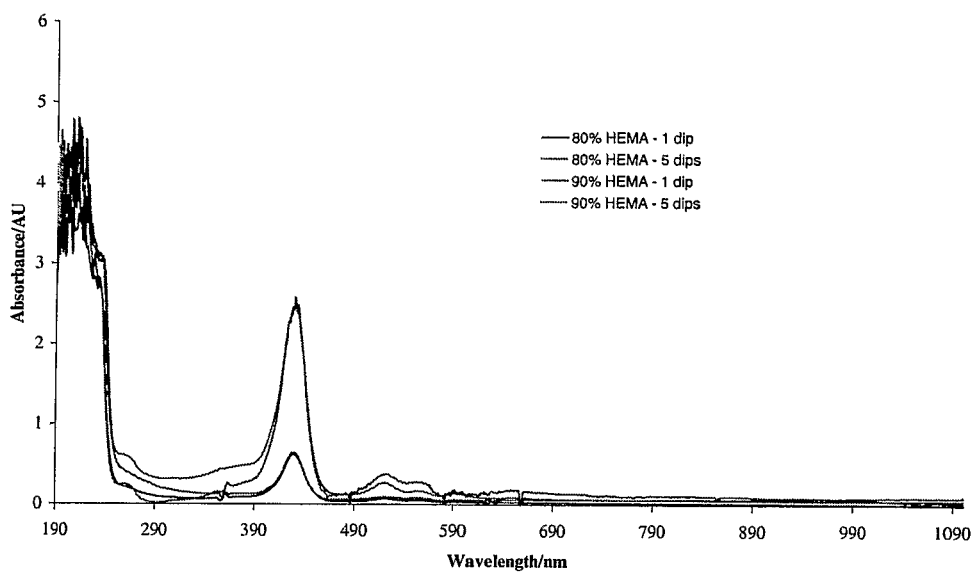
FIG. 2 illustrates UV-Vis spectra of 80% and 90% prewetted copolymers on dipping in a 100 mcg/ml aqueous solution.
Figure 3:
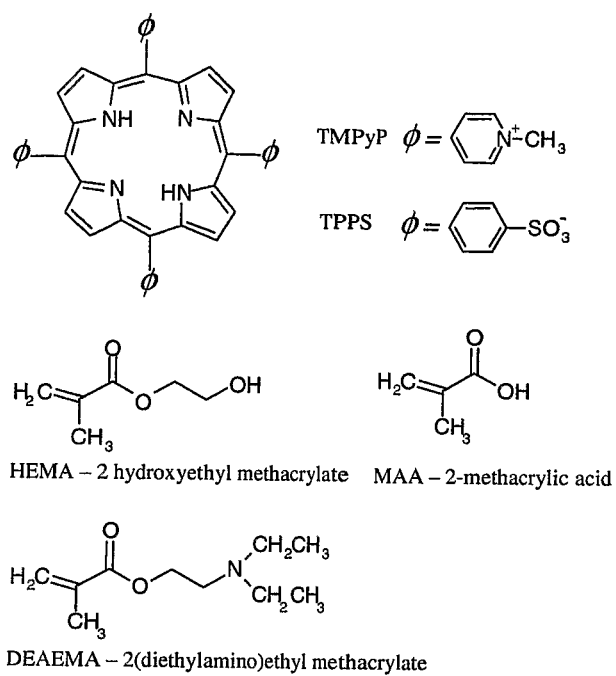
FIG. 3 illustrates five embodiments of the structures of porphyrins and monomers incorporating porphyrin sensitizers as thin coatings on a material.

As shown in FIG. 1 systems of type (a) of FIG. 1 are based on the electrostatic interaction between the cationic tetra-4-N-methylpyridinium porphyrin (TMPyP), which has an overall +4 charge and the anionic copolymer poly(methacrylic acid-co-hydroxyethylmethacrylate) or between the anionic tetra-4-sulfonato-phenylporphyrin (TPPS), which has an overall −4 charge and the cationic copolymer poly(diethylaminoethylmethacrylate-co-hydroxyethylmethacrylate). In both cases strong binding between porphyrin and hydrogel may be provided such that if the hydrogel is immersed in an aqueous solution of the porphyrin, the porphyrin will bind only at the first point of contact with the hydrogel (i.e. the surface); it will therefore not penetrate deep into the hydrogel interior.

Coating a biomaterial using this method may be appropriate to provide intra-ocular lenses that are stable and have significant light-induced anti-bacterial properties.

Fluorescence microscopy studies indicate that the porphyrins preferentially localise in a surface layer at the polymer surface, which is where they are required to inhibit intra-ocular lens bacterial colonisation. When these polymers were challenged with a clinical isolate of *Staphylococcus aureus* taken from an intra-ocular lens retrieved from a patient, followed by irradiation with visible light, a significant reduction in the number of viable bacteria on the surface was observed after just 30 seconds illumination.

EXAMPLE 2

Incorporation of Sensitizer(s) Using Covalent Interaction

Referring to FIG. 1*b* biomaterials may be formed using hydrogels which are coated with copolymers of a standard monomer, 2-hydroxyethylmethacrylate (HEMA, a biocompatible hydrogel that has found widespread use as an ocular biomaterial), with a vinyl-functionalised porphyrin.

The preparation involves dip- or spin-coating a mixture of HEMA, porphyrin and initiator onto the biomaterial surface.

Heating initiates free-radical polymerisation to give a material with porphyrin covalently bound at the surface layer.

EXAMPLE 3

Porphyrin Impregnated Material Studies

Microbiological activity of porphyrin-impregnated materials has been studied.

Based on the triplet results, 90% HEMA prewetted and dipped for 60 s in a 100 mcg/mL TMPyP solution was tested.

Portions of material, cut into 1 $cm^2$ pieces, were placed on sterile hypodermic needles which were then placed inside sterile McCartney bottles. The materials to be dipped in porphyrin solution were then dipped in the 100 mcg/mL solution in a McCartney bottle and then rinsed with phosphate buffered saline (pH 7.4) to remove any excess porphyrin from the surface.

Enough S. epidermidis culture ($2.62 \times 10^8$ cfu/mL bioburden) was added to completely cover the materials in the McCartney bottles which were then placed in an orbital incubator shaker. The materials were removed after 4 hours.

The number of organisms adhering was subsequently determined using the following method.

Using sterile forceps the needles were removed and placed in a McCartney bottle containing approximately 20 mL ¼ strength Ringers solution and shaken for 30 s.

This procedure was repeated three times in all to remove any non-adhered material. Each disc was placed in a separate test tube containing 10 mL ¼ strength Ringers solution and one of the controls left in lab light and temperature.

The other control and the porphyrin impregnated material were positioned in the light produced from the 4×250 W set-up for 1 hour.

The adhered organisms were then removed and counted.

The tubes containing the samples were each sonicated for 5 minutes and vortexed for 30 s. The liquid was then decanted from each test tube into another empty sterile test tube. Serial dilution and plating out onto Müller-Hinton agar were then performed using the Miles and Misra method. The plates were then incubated overnight before calculating the numbers of organisms adhering to each $cm^2$ piece of material.

Viable count–S. epidermidis=$2.62 \times 10^8$ cfu/mL

Results

Control material, daylight=$1.13 \pm 1.02 \times 10^5$ cfu/$cm^2$

Control material, intense light set-up=$1.14 \pm 0.42 \times 10^4$ cfu/$cm^2$

Porphyrin impregnated material=$5.33 \pm 0.21 \times 10^3$ cfu/$cm^2$, representing 95.3% kill relative to control material exposed to daylight.

These results are expressed as the mean and standard deviation of 5 replicates. The porphyrin-impregnated material appears to show a significant reduction in adherence when compared to control. The light set-up itself appears also to have some toxic effect on the viability of the bacteria.

EXAMPLE 4

Using the same material, same porphyrin and same incorporation conditions, but challenged with a lower inoculum of $5.05 \times 10^3$ cfu/mL S. epidermidis, samples containing porphyrin kept in the dark showed a reduction in adhered organisms of 97.0% relative to a control sample exposed to daylight, and samples containing porphyrin and exposed to strong light showed a reduction compared to the control of 100% (i.e. complete kill was achieved).

EXAMPLE 5

Preparation of polymer matrices including charged porphyrins at their surface and which are capable of generating $^1O_2$ at the point of bacterial attachment A range of copolymer compositions were investigated to determine if inclusion of larger proportions of a charged monomer had a significant effect on the porphyrin binding.

Copolymers were produced by free radical polymerisation in the presence of crosslinkers, as previously described by (Jones D. S.; Bonner, M. C.; Akay, M.; Keane, P. F.; Gorman, S. P. *Journal of Materials Science Materials in Medicine*, 1997, 8, 713.; Jones, D. S.; McLaughlin, D. W. J.; McCoy, C. P.; Gorman, S. P. *Biomaterials*, 2005, 26, 1761; Jones, D. S.; Andrews, G. P.; Gorman, S. P. J. *Pharmacy and Pharmacology*, 2005, 57, 1251.)

Copolymers composed of a variety of compositions of HEMA and MAA were prepared by mixing the required amounts of HEMA, MAA, crosslinking agent (EGDMA, ethylene glycol dimethacrylate, 1% w/w) and the initiator (benzoyl peroxide (BPO), 0.4% w/w) in a flat-bottomed beaker. The mixture was mechanically stirred until the benzoyl peroxide had fully dissolved. The solution was then injected into a mould, made using medical grade tubing placed in between two sides of silicone release liner held together by two glass plates. The plate moulds were then placed in a fan-assisted oven maintained at 90° C. for two hours, during which time the polymerisation reaction occurred. This procedure generated flat sheets which were at least 100 mm×100 mm and whose thickness was controlled by the plate spacing (typically ca. 0.75 mm). The cationic copolymers of DEAEMA and HEMA were synthesised using a similar method; AIBN (2,2-azobis(2-methylpropionitrile) (1% w/w) was used instead of BPO as the initiator and the polymerisation was in an oven maintained at 60° C. for 18 hours. On removal from the moulds, the films were washed with deionised water, cut into samples of a convenient size (ca. 10×20 mm) and were then immersed in deionised water for 14 days to remove any unreacted monomer before use.

Porphyrins were loaded into the polymer films by immersing the 10×20 mm film samples for 60 seconds into high concentration (1-100 µg/ml, depending on loading level required) solutions of the complementary porphyrin (TMPyP for MAA:HEA, TPPS for DEAEMA:HEMA). Fine control of the loading was achieved by repeating the immersion process. The polymer films were pre-soaked in Tris (tris(hydroxymethyl)aminoethane) buffer before being treated, since this circumvented any potential complications which might be associated with loading porphyrin into dry polymer samples where solvent ingress and polymer swelling would necessarily occur in parallel with incorporation of the sensitizer.

Electronic absorption spectra were recorded on a Hewlett Packard HP8453 diode array single beam spectrophotometer with 2 nm resolution over a 190-820 nm wavelength range. Fluorescence spectra were measured using a Perkin Elmer LS55 luminescence spectrometer equipped with a R928 photomultiplier.

For the transient absorption and singlet oxygen studies, the second harmonic output from a Q-switched Nd:YAG laser was used as the excitation source and the sample was mounted at 450 to the excitation beam. A pulse energy of 1 mJ was used for the measurements to avoid burning the sample. For transient absorption measurements, light from a xenon arc lamp (Applied Photophysics Ltd., 150 W) traveling at 90° to the excitation beam was directed through the sample and into a monochromator (Applied Photophysics Ltd., 1200 gr/mm grating.) fitted with an IP28 photomultiplier detector connected to a sampling oscilloscope (Tektronix TDS 3032). A 532 nm holographic notch filter (Kaiser Optical Systems Inc.) was mounted in front of the monoochromator entrance slit to reduce the effect of laser scatter on the signal. Processing of the data was carried out using SigmaPlot for Windows (Version 8.0).

The $^1O_2$ detection system was a liquid-nitrogen-cooled Indium Gallium Arsenide (InGaAs) detector (Judson Technologies Inc, Montgomeryville, Pa., type J22D-M204-R01M-60-1.7) with a 1 mm² active area. The detector output was amplified using a Judson PA9 pre-amplifier and collected using a Tektronix TDS 3032 oscilloscope. To obtain acceptable signal-to-noise ratios 512 decays were summed for each reading. To minimise the effect of any inhomogeneity in the sample, readings from 8 different points were averaged, The singlet oxygen emission at 1270 nm was separated from the 1064 nm fundamental laser emission and other spurious emissions by use of a 1200 nm long pass filter (LP1200) and a 1292 nm band pass filter (BPO-1292-80), both supplied by Spectrogon UK Ltd.

Confocal laser scanning microscopic (CLSM) examination of samples was carried out with a Leica TCS SP2 confocal laser scanning microscope. After focusing, the sample surface was excited using the 514 nm line from a Ar/ArKr laser and fluorescence emission data collected over the range 600-720 nm. Fluorescence emission micrographs which showed summed photomultiplier intensities across the full wavelength range detected were recorded but are not shown here since displaying the data as intensity versus depth into the sectioned film is more appropriate for measuring penetration depths.

Contact angles of the copolymers were measured using a First Ten Angströms FTA 200 video-based contact angle analyser. All measurements were carried out at room temperature on hydrated materials in a three-phase system consisting of deionised water/buffered solution, the surface of the material and a bubble of air. The sample was placed on top of two inert plastic supports in the liquid chamber and a bent needle syringe shaped in the form of a "J" was used to dispense air bubbles with a volume of 20 μL. These adhered to the lower surface of the sample and were recorded and measured using the instrument's internal video capture system and software. The contact angle between the air and the sample surface, $\theta_{air}$ was measured for 10 bubbles and the mean value of the complementary angle, $\theta_{buffer}$, was calculated.

Electrostatic binding of porphyrins to the surfaces of polymers was tested as this method of production would be more convenient to produce material and attachment of the porphyrin at the surface of a material would be advantageous as such material would be capable of generating $^1O_2$ at the point of potential bacterial attachment of generating material.

Samples of polymer film were dipped into a high concentration solution of a complementary porphyrin (TMPyP for MAA:HEA, TPPS for DEAEMA:HEMA) and initial tests showed that immersion for even a few seconds resulted in binding of porphyrin to the polymer. This was as observed as a distinct yellow/orange tint in the polymer file that could not be removed even by vigorous washing.

Systematic studies were conducted to determine those factors important in determining the properties of copolymer films whose surfaces have been modified by this simple route. Many of the features of the sample preparation and characterization were determined to be similar for both anionic and cationic porphyrin/copolymer combinations. In view of this, the preparation and characterization of cationic TMPyP in MAA:HEMA system is fully described below and description for the TPPS/DEAEMA:HEMA system is only provided in relation to those features which were significantly different from the cationic analogue.

Loading of Porphyrins into Copolymer Films

UV/Vis spectra of all the porphyrin-loaded films were dominated by the porphyrin content and provided a useful method for determining total porphyrin loading in μg cm⁻² (measurement of local concentration, which varied with distance from the surface). Initial experiments using the MAA:HEMA copolymers were carried out on samples between 0:100/MAA:HEMA and 100:0/MAA:HEMA. However, the inventors determined that samples with >30% MAA were cloudy. Subsequent studies were confined to the transparent polymers with 0, 10, 20 and 30% MAA.

To prepare samples with very different porphyrin loadings, to allow a range of characterization methods to be used, gross concentration changes to the porphyrin solution were made.

Whilst flash photolysis measurements could be carried out on MAA:HEMA samples which were dipped 5 times into 10 μg/ml solutions of TMPyP, higher loadings, prepared in the same way but using 100 μg/ml solutions, were needed for singlet oxygen measurements. This higher loading method gave films with a peak absorbance ca. 1-2 at $\lambda_{max}$, which were also suitable for UV/vis absorption measurements.

It is well known that $\lambda_{max}$ of the Soret band of tetra-aryl porphyrins shifts in different chemical environments, for example $\lambda_{max}$ of $H_2TPPS$ shifts 2 nm on incorporation in cationic functionalized polystyrene beads and TMPyP shows a 22 nm bathochromic shift (422 nm-444 nm) on binding to poly(dG-dC). However, it can be difficult to associate these shifts to particular binding motifs since they may be associated with non-specific effects, such as a modification of the polarity of the medium or they may arise from weak electronic interactions between the porphyrin substituents and binding groups on the host. In addition, the formation of dimers/oligomers in the polymer film or dissociation of aggregates which were present in solution but not in the films could also give significant shifts in the porphyrin absorption.

Figure 4:
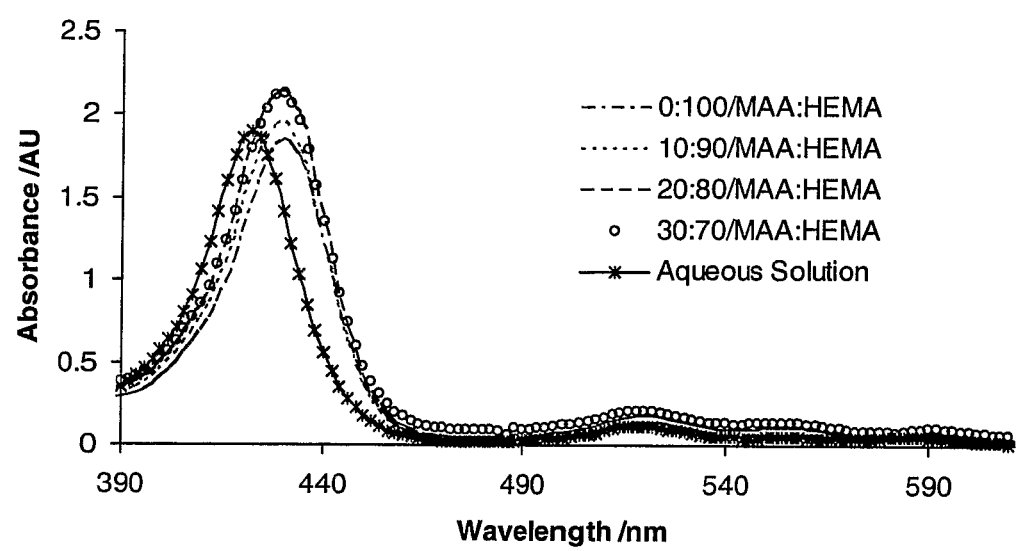
FIG. 4 illustrates UV/Vis absorption spectra of TMPyP in MAA:HEMA copolymers on dipping in 100 µg/ml porphyrin solution.

FIG. 4 shows that $\lambda_{max}$ for TMPyP in MAA:HEMA shifts slightly to the red when it is bound to MAA:HEMA. (430 nm for bound porphyrin, 424 nm for TMPyP in aqueous solution). The shift was found to be essentially identical for all the polymer compositions implying that the environment around the bound porphyrins was similar at all compositions. Similarly, the uptake, as determined from the absorbance at $\lambda_{max}$, was also very similar for each of the polymers (see FIG. 4). A slightly higher absorbance was observed for the 30 and 20% MAA than the 10% but, somewhat surprisingly, the extent of incorporation into the 100% HEMA was almost as high as in the MAA:HEMA copolymers, despite the fact that that no anionic groups were deliberately introduced into the polymer. It is possible that incomplete esterification of the HEMA resulted in a small population of residual uncapped anionic binding sites even in "100%" HEMA samples, which is consistent with the similar shift in $\lambda_{max}$ observed in all the polymers studied. The release studies discussed below do however suggest that the TMPyP was less strongly held in 100% HEMA than in the MAA:HEMA polymers.

Figure 5A:
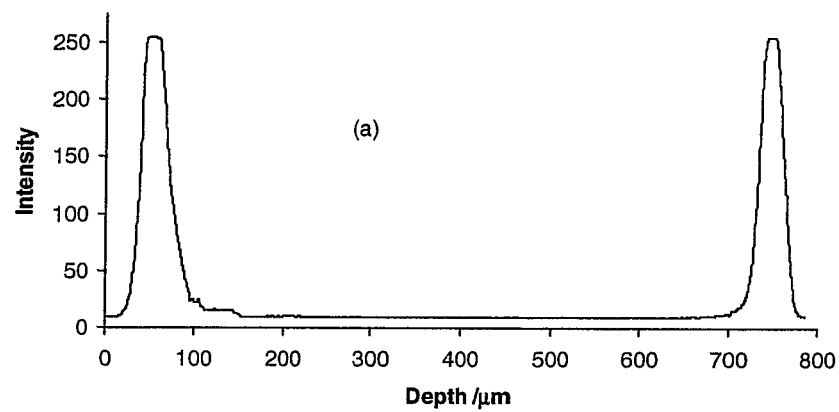
FIG. 5a illustrates the depth profiles of the fluorescence intensity of TMPyP in 20:80/MAA:HEMA films on dipping once in 100 µg/ml porphyrin solution.
Figure 5B:
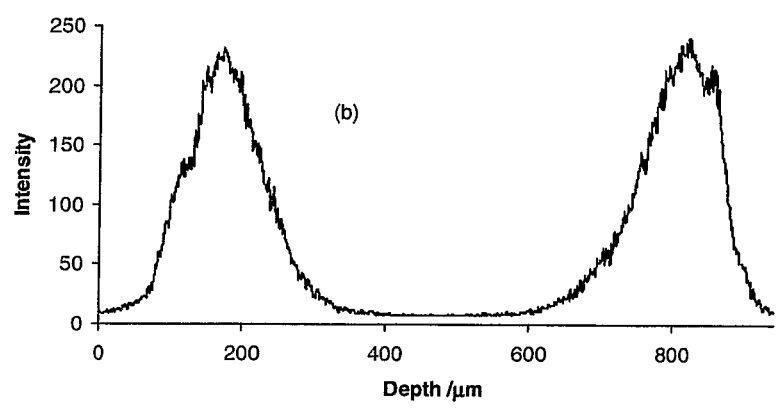
FIG. 5b illustrates the depth profiles of the fluorescence intensity of TMPyP in 20:80/MAA:HEMA films on dipping five times in 100 µg/ml porphyrin solution.
Figure 6:
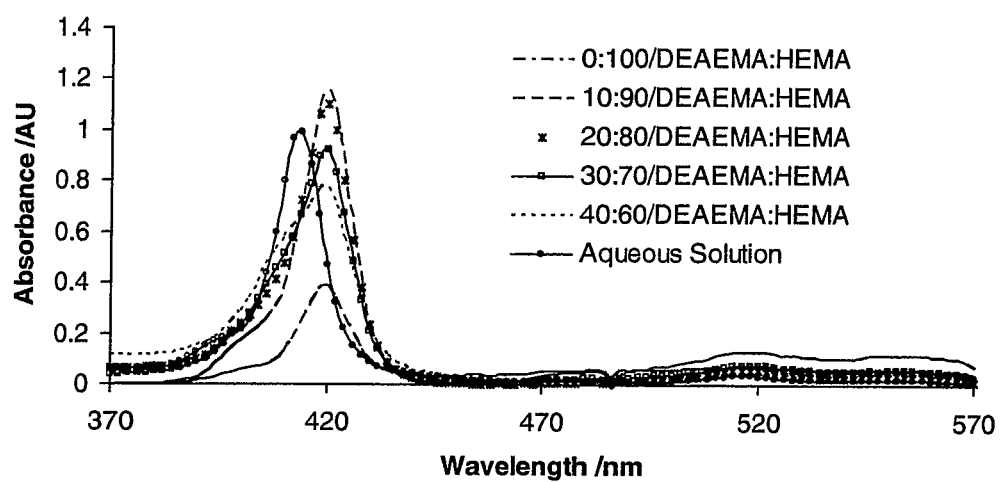
FIG. 6 illustrates UV/Vis absorption spectra of TPPS in DEAEMA:HEMA copolymers on dipping 5 times in 10 µg/ml porphyrin solution.

Since the samples were prepared by immersion of films into porphyrin solutions, initial incorporation must necessarily have been into surface layers, but it was not obvious whether the porphyrins would penetrate the films to a significant depth or would remain in a high concentration layer at the surface. Confocal laser fluorescence microscopy of MAA:HEMA films showed that after 1 immersion cycle the porphyrin was indeed localized in a <50 μm surface layer and there was no evidence for significant penetration of porphyrin from the surface to the core (FIG. 5(a)). Repeating the immersion cycle 5 times gave samples with increasing loading levels whose depth profiles showed evidence of an outer layer >100 μm which appeared to be saturated with porphyrin, deeper into the film the concentration decreased non-linearly over the next 50-100 μm (see FIG. 5(b)). This profile is consistent with a model where the initial porphyrins bind strongly to the outer layers of the polymer and subsequent porphyrins must diffuse through the growing saturated layer to find vacant binding sites. Release studies (see below) imply that it is difficult for any bound TMPyP to release, which rules out the alternative model where porphyrins penetrate the polymer through a series of binding/release steps.

The fluorescence profiles also allowed the porphyrin concentration within the films to be estimated. UV/vis absorption spectroscopy (FIG. 4) gave the loading per $cm^2$ of film, but this is a global value that does not take account of the inhomogeneous depth profile. However, the confocal fluorescence data (FIG. 5) for the 20:80/MAA:HEMA polymer, for example, shows that in the films prepared in this example the porphyrin can be regarded as confined to 2 layers ca. 180 μm thick which to a first approximation are uniformly loaded with TMPyP. Taken with the peak absorbance and assuming an extinction coefficient $2.26 \times 10^5$ $dm^3 mol^{-1} cm^{-1}$ gives a concentration in these surface layers of $2 \times 10^{-4}$ $mol\ dm^{-3}$. For all the MAA:HEMA compositions studied the extent of penetration by the porphyrin was found to be similar when similar loading conditions were used.

TABLE 1

Contact angles for MAA:HEMA copolymers of varying composition treated with TMPyP.

| Composition MAA:HEMA | θ° blank | θ° 100 μg/ml TMPyP | θ° 1 μg/ml TMPyP |
| --- | --- | --- | --- |
| 30:70 | 34.4 ± 2.5 | 23.8 ± 3.5 | 23.7 ± 0.6 |
| 20:80 | 41.6 ± 1.2 | 22.7 ± 1.4 | 24.1 ± 1.8 |
| 10:90 | 47.0 ± 4.3 | 24.5 ± 1.7 | 23.7 ± 3.1 |
| 0:100 | 48.3 ± 2.1 | 24.7 ± 2.8 | 25.8 ± 1.6 |

Contact angle measurements (Table 1) clearly show that the surface properties are established even at low TMPyP loading since the wide range of θ values observed for the blank polymers converge to single value of ca. 24° on first treatment and do not alter as the porphyrin loading is increased. It is interesting that, despite the significant variation in contact angle for the untreated polymers with different compositions, the treated samples all have the same contact angle. This suggests that the surface properties of the modified polymers are dominated entirely by the porphyrins, which can change the contact angle by up to 22°.

The general features of TPPS incorporation into DEAEMA:HEMA copolymers were similar to the TMPyP system described above. $\lambda_{max}$ of the polymer bound TPPS also showed a similar bathochromic shift compared to solution ($\lambda^{max}$=412 nm in solution, 420 nm in 10:90/DEAEMA:HEMA) but, as shown in FIG. 4, the 40:60/DEAEMA:HEMA showed clear evidence of two different types of binding with a shoulder on the Soret band at 410 nm, near the position of the solution $\lambda_{max}$. The occurrence of different binding domains within copolymers of this type is not unexpected.

TABLE 2

Contact angles for DEAMA:HEMA copolymers of varying composition treated with TPPS.

| Composition DEAEMA:HEMA | θ° Blank | θ° 100 μg/ml TPPS |
| --- | --- | --- |
| 30:70 | 32.2 ± 0.8 | 27.3 ± 1.3 |
| 20:80 | 36.4 ± 1.6 | 29.7 ± 2.8 |
| 10:90 | 41.3 ± 3.2 | 29.6 ± 3.7 |
| 0:100 | 48.0 ± 2.4 | 31.8 ± 0.2 |

One significant difference between the TPPS and TMPyP systems was the extent of sensitizer uptake for a given concentration of loading solution. With MAA:HEMA, dipping the films 5 times into 100 μg/ml solutions of TMPyP gave samples with absorbance ca. 2 at $\lambda_{max}$; with DEAEMA:HEMA loading with 100 μg/ml TPPS solutions gave very heavily doped dark red samples and much lower concentration (10 μg/ml) TPPS solutions were required to generate samples with an appropriate absorbance at $\lambda_{max}$. Confocal laser scanning microscopy also showed a significant difference in the distribution of porphyrin in the anionic and cationic polymer systems. In contrast to the MAA:HEMA polymers, where the TMPyP formed a band >150 μm deep, the 30:70/DEAEMA:HEMA showed remarkably little penetration of the TPPS into the body of the copolymer film, even after 5 immersions the porphyrin was confined to a narrow band (FWHM<20 μm) at the film's surface (see FIG. 7).

Without wishing to be bound by theory, the inventors consider that the initial binding of the charged polymers restricts the ingress of additional porphyrin so the adsorbed material remains concentrated near the surface (local porphyrin concentration is estimated as ca. $4 \times 10^{-3}$ $mol\ dm^{-3}$ i.e. >20× larger than TMPyP in the MAA:HEMA polymers).

Contact angle measurements (Table 2) show that binding the porphyrin to the surface does significantly alter the contact angle by up to 16° and that binding TPPS resulted in a near identical contact angle for all the polymer compositions investigated, irrespective of their untreated values. However, this behaviour cannot be directly linked to an unusually strong surface binding by TPPS because similar effects were observed for TMPyP in the MAA:HEMA system where the porphyrin penetrated much more deeply into the copolymer film.

Photophysical Studies

Transient absorbance difference (ΔA) measurements were carried out under oxygen-bubbled conditions and after degassing by nitrogen-bubbling for 20 minutes. $N_2$ bubbling is much less effective at removing oxygen than repeated freeze-pump-thaw cycles. However, $N_2$ bubbling was used in the present studies as freeze-pump-thaw was inappropriate for the polymer samples. The gross photophysical properties of TMPyP in MAA:HEMA polymers were similar to those of simple aqueous solution, the triplet had a ca. 1 ms lifetime in deoxygenated polymer which fell to ca, 3 μs under $O_2$ saturation. The solution phase values measured by the inventors are 161 μs under $N_2$ bubbling, falling to 436 ns under $O_2$.

The solution phase data were always pure simple exponential decays within experimental error, but the residuals from single exponential was found to fit to the decay curves of the polymer samples and showed that the traces were not single exponential. This fits with the polymers being microheterogeneous and the porphyrins therefore being located in a broad range of environments.

Under $N_2$-bubbled conditions the triplet signals could be fitted to two approximately equal intensity components with lifetimes ca, 350 and 1300 µs (see Table 3) although this was an approximation at best and the residuals to this biexponential fit showed some structure, despite the $R^2$=0.99 (FIG. 8). It is likely that numerous different environments exist within a single polymer sample and the values of the fit give only an approximate indication of the range of lifetimes present and the relative proportions of longer- and shorter-lived components. Similarly, in the oxygen-bubbled polymers the lifetimes were not single exponential, although in this case there was a single dominant shorter component (ca. 90% of the signal) with $\tau$=3 µs and a minor longer-lived component with a significantly longer lifetime of 20 µs. Again, whilst not wishing to be bound by theory, the inventors consider this longer lived component arose from porphyrins which lay within domains where $O_2$ has low solubility and/or diffusion rates. No evidence of a systematic change in the relative contribution of these two components with changing polymer composition was detected.

TABLE 3

Transient absorbance lifetime data for porphyrin-treated copolymer samples and simple aqueous solutions of the same porphyrins.

| Material Composition | Conditions | $\tau_1$/µs (%) | $\tau_2$/µs (%) |
|---|---|---|---|
| MAA:HEMA | | | |
| 30:70 | $N_2$ bubbled | 230.1 ± 71.8 (47) | 1414.5 ± 142.0 (53) |
|  | $O_2$ bubbled | 2.9 ± 0.04 (87) | 23.7 ± 0.7 (13) |
| 20:80 | $N_2$ bubbled | 289.8 ± 104.5 (58) | 1113.6 ± 165.2 (42) |
|  | $O_2$ bubbled | 2.8 ± 0.1 (90) | 26.2 ± 4.1 (10) |
| 10:90 | $N_2$ bubbled | 487.5 ± 76.7 (70) | 1388.3 ± 228.8 (30) |
|  | $O_2$ bubbled | 2.8 ± 0.1 (92) | 37.9 ± 1.2 (8) |
| 0:100 | $N_2$ bubbled | 1097.8 ± 4.1 | |
|  | $O_2$ bubbled | 3.5 ± 0.005 (94) | 13.5 ± 0.07 (6) |
| Solution | $N_2$ bubbled | 161.0 ± 4.51 | |
|  | $O_2$ bubbled | 0.436 ± 0.00062 | |
| DEAEMA:HEMA | | | |
| 30:70 | $N_2$ bubbled | 378.1 ± 2.6 (47) | 1182.4 ± 34.2 (53) |
|  | $O_2$ bubbled | 310.2 ± 8.4 (46) | 1163.4 ± 46.7 (54) |
| 20:80 | $N_2$ bubbled | 471.3 ± 8.3 (33) | 1370.0 ± 10.1 (67) |
|  | $O_2$ bubbled | 383.5 ± 10.6 (30) | 1127.6 ± 62.7 (70) |
| 10:90 | $N_2$ bubbled | 497.0 ± 9.2 (51) | 1157.6 ± 38.7 (49) |
|  | $O_2$ bubbled | 302.5 ± 60.4 (31) | 1100.4 ± 88.7 (69) |
| 0:100 | $N_2$ bubbled | 891.5 ± 6.7 (95) | 2280.9 ± 247.65 (5) |
|  | $O_2$ bubbled | 3.22 ± 0.02 (92) | 14.34 ± 3.07 (8) |
| Solution | $N_2$ bubbled | 227.5 ± 6.1 | |
|  | $O_2$ bubbled | 0.760 ± 0.0023 | |

Solution data were fitted by a single exponential decay, polymer samples were fitted by two-component decays with lifetimes and % contribution to the total signal as shown.

The strong quenching of triplet TMPyP in the polymers by molecular oxygen shows that even the porphyrins that lie deep within the polymers are exposed to $O_2$ (all lifetimes are reduced by >1 order of magnitude on $O_2$ bubbling). For the purposes of antimicrobial activity it is only the surface which is important, but the fact that underlying porphyrins are also quenched is useful as it means that heavily doped samples gave more $^1O_2$ than samples with low loadings.

Experiments conducted using an InGaAs detector for direct detection of $^1O_2$ fluorescence at 1270 nm determined that TMPyP loaded MAA:HEMA copolymers give a strong emission signal at 1270 nm even under degassed conditions. This emission showed a bandwidth-limited rise and decay (2.5 µs and 3.5 µs, respectively) and did not appear to be due to an impurity in the polymer since it was also observed for TMPyP in simple aqueous solution, while experiments on undoped polymer showed no signal.

Figure 7:
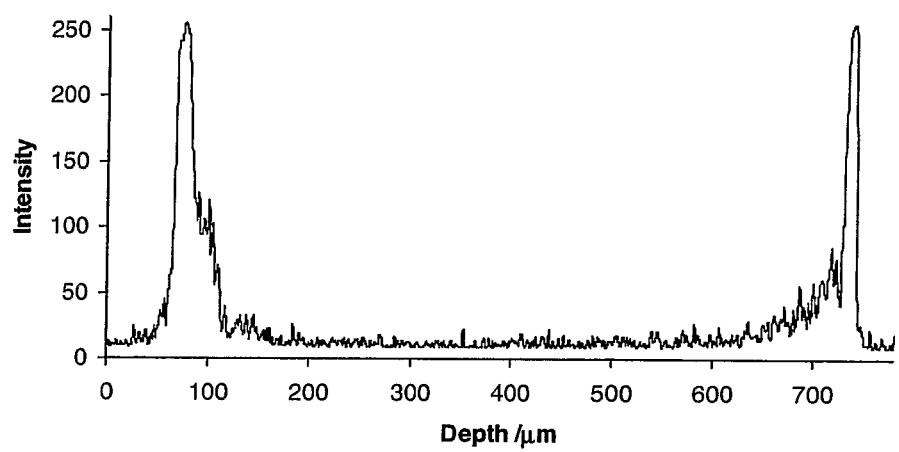
FIG. 7 illustrates depth profiles of the fluorescence intensity of a TPPS 30:70/DEAEMA:HEMA film on dipping in 100 µg/ml porphyrin solution.

Although the origin of the emission signal is unclear it was previously found that if $D_2O$ was used as the solvent the increased $^1O_2$ lifetime (62 µs vs. 3 µs in $H_2O$) allowed the $^1O_2$ signal to be separated from the much shorter emission signal. Using this approach, the polymers prepared were pre-wetted in buffer prepared with $D_2O$ and dipped in porphyrin solutions also prepared from $D_2O$. FIG. 7 shows $^1O_2$ emission from 4 doped polymer samples and from a solution which was absorbance matched. The solution phase, 0:100/MAA:HEMA and 10:90/MAA:HEMA samples show fluorescence yields (measured after the fast decaying initial emission) identical within the ca. 20% experimental uncertainty of the measurements. Following the rapid component, the traces show single exponential decay with lifetimes of 62 µs (solution) and 35 µs (polymer). The shorter lifetime in the polymer shows that the $^1O_2$ is not generated and retained within simple solvent pockets in the polymer, but instead it must be perturbed by interaction with the host.

Similar results would have been expected for the higher MAA content polymer samples but it was found that the intensity of the $^1O_2$ signal following the initial fast transient was only ca. 50% that of the other polymer samples, although the initial signal heights were the same with all the polymers studied. These observations are consistent with an additional fast decay channel being present in the high MAA polymers.

Overall, the data for TMPyP in MAA:HEMA suggest that loading water-soluble porphyrins into swellable acrylate-based gels leads to only minor perturbation in the photophysical and $^1O_2$ generating properties of their excited states. At first sight the data for the complementary DEAEMA:HEMA polymers doped with TPPS (Table 3) appear to be similar to the TMPyP system. Under nitrogen bubbled conditions the absorbance difference data for TPPS in DEAEMA:HEMA could be fitted to biexponential decays of approximately similar amplitude with lifetimes of ca. 400 and 1200 µs, the corresponding values for TMPyP were ca. 350 and 1300 µs. Similarly, the excited lifetimes of TPPS in solution and pure HEMA (where no electrostatic binding is expected) both fell dramatically, as expected, when $O_2$ was bubbled through initially degassed samples, in both cases falling by ca. 300× e.g. from 891 µs to 3 µs for HEMA.

It was found that with 10%-30% DEAEMA samples the excited state TPPS lifetimes were barely reduced at all on oxygen bubbling. For 10:90/DEAEMA:HEMA under standard loading conditions (5 immersions in 10 µg/ml TPPS, absorbance at $\lambda_{max}$~2) the two component biexponential fit gave lifetime reductions of the two components of 1158 to 1100 µs and 497 to 303 µs and similar reductions were also observed for the 20:80 and 30:70 copolymer samples. Bearing in mind the ca. 300× lifetime reduction observed on $O_2$ bubbling of 0:100/DEAEMA:HEMA (i.e. pure HEMA) samples, it is remarkable that with addition of just 10% of the DEAEMA copolymer in 10:90/DEAEMA:HEMA the lifetime of the longer-lived component was effectively unchanged on $O_2$ bubbling and the shorter component was reduced by a factor <2×.

It appears that in these copolymers the sensitizer which gives rise to the longer component in degassed conditions is located in domains where $O_2$ quenching is effectively prevented either by slow diffusion or low solubility in those regions. The porphyrins which have a shorter lifetime under degassed conditions are obviously in a different chemical environment and this is also reflected in the small extent of quenching which is observed on $O_2$ bubbling. A difference in the $O_2$ quenching efficiency was also observed for the TMPyP system in that a nominally biexponential degassed sample gave a nominally biexponential quenched trace. However, for the TMPyP system $O_2$ bubbling led to very large lifetime changes, so that in 10:90/MAA:HEMA even the longer component in the quenched sample had a lifetime (38 μs) which was >10× shorter than the short lived (488 μs) component of the degassed sample. Consistent with these observations, it was found that none of the TPPS/DEAEMA:HEMA systems gave detectable $^1O_2$ emission signals at 1270 nm, although the $\phi(^1O_2)$ for TPPS in solution is 0.6717 and TPPS in 100% HEMA did give a weak signal, consistent with the significant lifetime reduction that is observed when it is $O_2$ bubbled.

Confocal fluorescence measurements (FIG. 7) show that the TPPS initially binds at the exterior but, in contrast to the TMPyP system, further immersions in the doping solution do not result in the TPPS diffusing through the previously modified layer before ultimately binding deeper into the interior. Instead, even at very high doping levels the porphyrin remains confined within a thin surface layer. Without wishing to be bound by theory, the inventors consider that it is probable that strong cross-linking of the polymer chains by the polyanionic TPPS reduces diffusion of TPPS through previously-doped polymer regions. Similarly, such crosslinking may also be responsible for reducing the oxygen permeability of the doped TPPS films to such an extent that oxygen quenching is dramatically reduced. Previous studies on meso-sulphonatophenyl porphyrin covalently bonded to poly(vinyl alcohol) found that oxygen quenching, which was efficient in solution, was strongly reduced in dry porphyrin-modified PVA films which have very low oxygen permeability.

Release Kinetics

Release kinetics were recorded by immersing the porphyrin-doped polymer samples in buffer and withdrawing 1 ml aliquots at weekly intervals. Porphyrin concentration in the aliquots was then measured fluorimetrically ($\lambda_{ex}$=423 nm, $\lambda_{em}$=685 nm for the MAA:HEMA systems; $\lambda_{ex}$=413 nm, $\lambda_{em}$=645 nm for the DEAEMA:HEMA systems).

TABLE 4

Cumulative release data for TMPyP from MAA:HEMA copolymers of varying composition.

| Composition MAA:HEMA | % TMPyP released |
|---|---|
| 30:70 | 9.2 ± 1.1 |
| 20:80 | 8.6 + 0.5 |
| 10:90 | 7.4 + 1.4 |
| 0:100 | 16.3 ± 1.9 |

Data were measured fluorimetrically over a 10 week interval.

The data for the MAA:HEMA co-polymers are summarized in Table 4, which gives values for the cumulative release. Consistent with the expectation that the TMPyP will be less strongly held in the 100% HEMA polymer than in the MAA-treated polymers, where electrostatic interaction is anticipated, the 0:100/MAA:HEMA polymer shows almost twice as much release as the 10-30% MAA copolymers. The release kinetics (not shown) are also different for the 100% HEMA and the 10-30% MAA polymers, in the former most of the 16% release is in the first week while in the latter systems there is a smaller initial release (ca. 4%) followed by a gradual increase to the final (10 week) value which is still less than 10% of the bound porphyrin.

In contrast, negligible release was detected from the DEAEMA:HEMA co-polymers suggesting that the porphyrin is very tightly bound within this polymer system, which is consistent with the confocal fluorescence measurements. Similarly, the large release from the 0:100/DEAEMA:HEMA copolymer (23.9±6.4% over the 10 week period) is expected because no cationic groups were introduced to electrostatically bind the anionic porphyrin.

For TMPyP in MAA:HEMA copolymer matrices it has been determined that the lifetimes of the excited triplet state porphyrins were slightly longer than the solution values and although biexponential (or pseudo-biexponential) decay was observed this is not unusual for sensitizers bound in microheterogeneous hosts. Similarly, TMPyP in MAA:HEMA copolymers was strongly quenched by oxygen and the samples showed $^1O_2$ emission, this $^1O_2$ was generated at, or near, the surface (the porphyrin penetrated <200 μm) and its lifetime was similar to that in aqueous solution. In contrast, TPPS in DEAEMA:HEMA copolymers was unexpectedly resistant to oxygen quenching. In degassed samples the photophysical behavior was similar to that of TMPyP but introduction of oxygen had only a very small effect on the triplet lifetimes and no $^1O_2$ emission could be detected. This unusual behaviour appears to be associated with the strong binding of the porphyrin to the host which, although it does not perturb the photophysical properties of the porphyrin per se, does restrict access by oxygen.

It will be appreciated by those skilled in the art that suitable sensitizers as known in the art could be used to replace those as specifically recited herein. Further, any suitable polymers could be utilised to provide a material on or in which a suitable sensitizer may be provided

The invention claimed is:

1. A material comprising a biocompatible polymer having a shape or structure and at least one sensitizer localized at a surface of the polymer by electrostatic bonding, hydrogen bonding, or Van der Waals forces, the sensitizer providing a coating layer on the surface of the polymer wherein no surface of at least one polymer is chemically modified.

2. The material of claim 1, wherein the coating layer has a thickness of from 10 nm to 1 mm.

3. The material of claim 1, wherein the sensitizer produces highly reactive singlet oxygen $^1O_2$ following exposure of the sensitizer to electromagnetic radiation.

4. The material of claim 1, wherein the sensitizer is selected from the group consisting of: phthalcyanine, metallophthalocyanine, sulphonated phthalocyanine, sulphonated metallocyanine, chlorine, texaphyrin, sapphyrin, purpurin, porphyrin, methylene blue, rose bengal, and any combination thereof.

5. The material of claim 1, wherein the sensitizer is porphyrin.

6. The material of claim 5, wherein the porphyrin is selected from the group consisting of: protoporphyrin IX, tetra-4-N-methylpyridinium porphyrin (TMPyP), tetra-4-sulfonato-phenyl porphyrin (TPPS), tetra(4N,N,N-trimethyl-anilinium)porphine tetrachloride (TMAP), hematoporphyrin derivative (HpD), purified fractions of hematoporphyrin derivative, photofrin, and any combination thereof.

7. The material of claim 5, wherein the porphyrin is selected from the group consisting of tetra-4-N-methylpyrinium porphyrin (TMPyP) and tetra-4-sulfonato-phenyl porphyrin (TPPS).

8. The material of claim 1, wherein the polymer is a natural biopolymer or a synthetic polymer.

9. The material of claim 1, wherein the polymer is biostable.

10. The material of claim 1, wherein the polymer is a hydrogel.

11. The material of claim 10, wherein the hydrogel is selected from the group consisting of poly(methacrylic acid-co-hydroxyethylmethacrylate), poly(diethylaminoethylmethacrylate-co-hydroxyethylmethacrylate), poly(hydroxyethlmethcacrylate-co-protoporphyrin), and any combination thereof.

12. The material of claim 1, wherein the sensitizer provides increased antimicrobial activity following exposure of the sensitizer to electromagnetic radiation of wavelength in the range 200 nm to 750 nm.

13. The material of claim 1, wherein the polymer having a shape or structure is tubing.

14. The material of claim 1, wherein the polymer having a shape or structure has a honeycomb structure 15. The material of claim 1, wherein the polymer having a shape or structure comprises beads.

* * * * *